United States Patent
Cho et al.

(10) Patent No.: US 12,374,462 B2
(45) Date of Patent: Jul. 29, 2025

(54) METHOD FOR DIAGNOSING CANCER AND PREDICTING CANCER TYPE BY USING TERMINAL SEQUENCE MOTIF FREQUENCY AND SIZE OF CELL-FREE NUCLEIC ACID FRAGMENT

(71) Applicant: GC GENOME CORPORATION, Gyeonggi-do (KR)

(72) Inventors: Eun Hae Cho, Gyeonggi-do (KR); Tae-Rim Lee, Gyeonggi-do (KR); Sook Ryun Park, Seoul (KR)

(73) Assignee: GC GENOME CORPORATION, Yongin-si (KR)

( * ) Notice: Subject to any disclaimer, the term of this patent is extended or adjusted under 35 U.S.C. 154(b) by 6 days.

(21) Appl. No.: 18/171,360

(22) Filed: Feb. 19, 2023

(65) Prior Publication Data

US 2023/0260655 A1 Aug. 17, 2023

Related U.S. Application Data

(63) Continuation of application No. PCT/KR2022/007651, filed on May 30, 2022.

(30) Foreign Application Priority Data

May 28, 2021 (KR) .................. 10-2021-0068891

(51) Int. Cl.
  *G16H 50/20* (2018.01)
  *G16B 30/10* (2019.01)
  *G16B 40/00* (2019.01)

(52) U.S. Cl.
  CPC .............. *G16H 50/20* (2018.01); *G16B 30/10* (2019.02); *G16B 40/00* (2019.02); *G01N 2800/7028* (2013.01)

(58) Field of Classification Search
  CPC . G16H 50/20; G16B 30/10; G01N 2800/7028
  See application file for complete search history.

(56) References Cited

U.S. PATENT DOCUMENTS

| | | | |
|---|---|---|---|
| 7,244,567 B2 | 7/2007 | Chen et al. | |
| 10,975,431 B2* | 4/2021 | Velculescu | C12N 15/1068 |
| 2005/0088236 A1 | 4/2005 | Matsumoto et al. | |
| 2006/0246497 A1 | 11/2006 | Huang et al. | |
| 2006/0275779 A1 | 12/2006 | Li et al. | |
| 2007/0087362 A1 | 4/2007 | Church et al. | |
| 2007/0194225 A1 | 8/2007 | Zorn | |
| 2019/0189242 A1 | 6/2019 | Angiuoli et al. | |

FOREIGN PATENT DOCUMENTS

| KR | 1020190036494 A | 4/2019 |
|---|---|---|
| KR | 101984611 B1 | 5/2019 |
| KR | 102084683 B1 | 2/2020 |
| KR | 1020200011471 A | 2/2020 |
| KR | 1020200087427 A | 7/2020 |
| KR | 1020200101106 A | 8/2020 |
| KR | 1020200108938 A | 9/2020 |
| WO | 2020125709 A1 | 6/2020 |

OTHER PUBLICATIONS

Alzubaidi et al. (Journal of Big Data, 2021 vol. 8:pp. 1-74).*
Ma et al. (Plos One, 2017. vol. 12:e0169231, pp. 1-18).*
Huang et al. (Cancer (2019) vol. 11:e-pp. 1-15) (Year: 2019).*
Jiang et al. (Cancer Discov 2020; 10:664-73) (Year: 2020).*
Trends Cancer. Apr. 2021 ; 7(4): 283-292 (Year: 2021).*
"Applied Biosystems, Carlsbad, California, USA", Applied Biosystems, 2009, Corona Lite Introduction 27 pages.
Branton, D., et al., "The potential and challenges of nanopore sequencing", Nature Biotechnology, 2008, pp. 1146-1153, vol. 26, No. 10, Publisher: Nature Publishing Group.
Butler, J., et al., "ALLPATHS De novo assembly of whole-genome shotgun microreads", Genome Research, 2008, pp. 810-820, vol. 18, Publisher: Cold Spring Harbor Laboratory Press.
Campagna, D., et al., "PASS a program to align short sequences", Bioinformatics, 2009, pp. 967-968; doi:10.1093/bioinformatics/btp087, vol. 25, No. 7, Publisher: Oxford University Press.
Chen Y., et al., "PerM: efficient mapping of short sequencing reads with periodic full sensitive spaced seeds", Bioinformatics, 2009, pp. 2514-2521; doi: 10.1093/bioinformatics/btp486, vol. 25, No. 19.
Clement, N.L., et al., "The GNUMAP algorithim unbiased probablistic mapping of oligonucleotides from next-generation sequencing", Bioinformatics, 2010, pp. 38-45, vol. 26, No. 1, Publisher: Oxford University Press.
De Bona, F., et al., "Optimal spliced alignments of short sequence reads", Bioinformatics, 2008, pp. i174-i180, vol. 24, No. 16, Publisher: Oxford University Press.
Eaves, H.L., et al., "MOM: maximum oligonucleotide mapping", Bioinformatics, 2009, pp. 969-970; doi. 10.1093/bioinformatics/btp092, vol. 25, No. 7, Publisher: Oxford University Press.

(Continued)

*Primary Examiner* — Lori A. Clow

(74) *Attorney, Agent, or Firm* — Knobbe, Martens, Olson & Bear, LLP

(57) ABSTRACT

Disclosed is a method for diagnosing cancer and predicting a cancer type using fragment end motif frequencies and sizes of cell-free nucleic acid, and more preferably, to a method for diagnosing cancer and predicting a cancer type by extracting nucleic acids from a biological sample to obtain sequence information, acquiring fragment end motif frequencies and sizes of nucleic acids based on the aligned reads, converting the fragment end motif frequencies and sizes of nucleic acids into vectorized data, inputting the vectorized data to a trained artificial intelligence model and analyzing a resulting calculated value. The method includes generating vectorized data and analyzing the same using an AI algorithm and thus is useful due to high sensitivity and accuracy thereof even in the case of low read coverage.

16 Claims, 7 Drawing Sheets

Specification includes a Sequence Listing.

(56) References Cited

OTHER PUBLICATIONS

Edwards, J.R., et al., "Mass-spectrometry DNA sequencing", Mutation Research, 2005, pp. 3-12, vol. 573, Publisher: Elsevier.

Fahlgren, N., "Computational and analytical framework for small RNA profiling by high-throughput sequencing", RNA, 2009, pp. 992-1002, vol. 15, Publisher: ResearchGate.

Gnirke, A., et al., "Solution hybrid selection with ultra-long oligonucleotides for massively parallel targeted sequencing", Nature Biotechnology, 2009, pp. 182-189, vol. 27, No. 2, Publisher: Nature America, Inc.

Hanna, G.J., et al., "Comparison of Sequencing by Hybridization and Cycle Sequencing for Genotyping of Human Immunodeficiency Virus Type 1 Reverse Transcriptase", Journal of Clinical Microbiology, 2000, pp. 2715-2721, vol. 38, No. 7, Publisher: American Society for Microbiology.

Hinton, G., et al., "Deep Neural Networks for Acoustic Modeling in Speech Recognition", IEEE Signal Processing Magazine, 2012, pp. 82-97, vol. 29, No. 6.

Homer, N., et al., "BFAST An Alignment Tool for Large Scale Genome Resequencing", PLoS One, 2009, e7767, vol. 4, No. 11, Publisher: www.plosone.org, 12 pages.

Jiang, H., et al., "SeqMap: mapping massive amount of oligonucleotides to the genome", Bioinformatics, 2008, pp. 2395-2396; doi:10.1093/bioinformatics/btn429, vol. 24, No. 20, Publisher: Oxford University Press.

Jiang, P., et al., "Plasma DNA End-Motif Profiling as a Fragmentomic Marker in Cancer, Pregnancy, and Transplantation", Cancer Discovery, 2020, pp. 664-673, vol. 10.

Kent, W.J., "BLAT—The Blast-Like Alignment Tool", Genome Research, 2002, vol. 12, No. 656-664, Publisher: Cold Spring Laboratory Press.

Kim, Y.J., et al., "ProbeMatch rapid alignment of oligonucleotides to genome allowing both gaps and mismatches", Bioinformatics, 2009, pp. 1424-1425; doi:10.1093/bioinformatics/btp178, vol. 25, No. 11, Publisher: Oxford University Press.

Krishnakumar, S., et al., "A comprehensive assay for targeted multiplex amplification of human DNA sequences", PNAS, 2008, pp. 9296-9310; www.pnas.org/cgi/doi/10.1073/pnas.0803240105, vol. 105, No. 27.

Langmead, B., et al., "Ultrafast and memory-efficient alignment of short DNA sequenes to the human genome", Genome Biology, 2009, doi:10.1186/GB-2009-10-3-r25, vol. 10, No. R25, 10 pages.

Lasken, R.S., "Single-cell genomic sequening using Multiple Displacement Amplification", Current Opinion in Microbiology, 2007, pp. 510-516, vol. 10, Publisher: Elsevier.

Li, H., et al., "Mapping short DNA sequencing reads and calling variants using mapping quality scores", Genome Research, 2008, pp. 1851-1858, vol. 18, Publisher: CSH Press.

Li, R., et al., "SOAP: short oligonucleotide alignment program", Bioinformatics, 2008, pp. 713-714; doi:10.1093/bioinformatics/btn025, vol. 24, No. 5, Publisher: Oxford University Press.

Li, H., et al., "Fast and accurate short read alignment with Burrows-Wheeler transform", Bioinformatics, 2009, pp. 1754-1760; doi:10.1093/bioinformatics/btp324, vol. 25, No. 14.

Li, R., et al., "SOAP2 an improved ultrafast tool for short read alignment", Bioinformatics, 2009, pp. 1966-1967; doi:10.1093/bioinformatics/btp336, vol. 25, No. 15, Publisher: Oxford University Press.

Li, H., et al., "Fast and accurate long-read alignment with Burrows-Wheeler transform", Bioinformatics, 2010, pp. 589-595; doi:10.1093/bioinformatics/btp698, vol. 26, No. 5.

Lunter, G, et al., "Stampy: A statistical algorithm for sensitive and fast mapping of Illumina sequence reads", Genome Research, 2011, pp. 936-939, vol. 21, Publisher: Cold Spring Harbor Laboratory Press.

Malhis, N., et al., "Slider-maximum use of probability information for alignment of short sequence reads and SNP detection", Bioinformatics, 2009, pp. 6-13; doi:10.1093/bioinformatics/btn565, vol. 25, No. 1.

Metzker, M.L., "Sequencing technologies—the next generation", Nature Reviews Genetics, 2010, pp. 31-46, vol. 11, Publisher: Macmillan Publishers Limited.

Muller, T., et al., "Non-symmetric score matrices and the detection of homologous transmembrane proteins", Bioinformatics, 2001, pp. S182-S189, vol. 17, No. 1, Publisher: Oxford University Press.

Ning, Z., et al., "SSAHA: A Fast Search Method for Large DNA Databases", Genome Research, 2001, pp. 1725-1729, vol. 11, Publisher: Cold Harbor Laboratory Press.

Ondov, B.D., et al., "Efficient mapping of Applied Biosystems SOLiD sequence data to a reference genome for functional genomic applications", Bioinformatics, 2008, pp. 2776-2777; doi:10.1093/bioinformatics/btn512, vol. 24, No. 23.

Porreca, G.J., et al., "Multiplex amplification of large sets of human exons", Nature Methods, 2007, pp. 931-936, vol. 4, No. 11, Publisher: Nature Publishing Group.

Prufer, K., et al., "PatMaN rapid alignment of short sequences to large databases", Bioinformatics, 2008, pp. 1530-1532; doi:10.1093/bioinformatics/btn223, vol. 24, No. 13.

Rumble, S.M., et al., "SHRiMP: Accurate Mapping of Short Color-spade Reads", PLoS Computational Biology, 2009, e1000386, vol. 5, No. 5, 11 pages.

Salmela, L., "Correction of sequencing errors in a mixed set of reads", Bioinformatics, 2010, pp. 1284-1290; doi:10.1093/bioinformatics/btq151, vol. 26, No. 10, Publisher: Oxford University Press.

Schatz, M. C., "CloudBurst: highly sensitive read mapping with MapReduce", Bioinformatics, 2009, pp. 1363-1369; doi:10.1093/bioinformatics/btp236, vol. 25, No. 11.

Shi, H, et al., "A Parallel Algorithim for Error Correction in High-Throughput Short-Read Data on CUDA-Enabled Graphics Hardware", Journal of Computational Biology, 2010, pp. 603-615; DOI:10.1089/cmb.2009.0062, vol. 17, No. 4, Publisher: Mary Ann Liebert, Inc.

Smith, A.D., et al., "Updates to the RMAP short-read mapping software", Bioinformatics, 2009, pp. 2841-2842; doi:10.1093/bioinformatics/btp533, vol. 25, No. 21, Publisher: Oxford University Press.

Tewhey, R., et al., "Microdroplet-based PCR enrichment for large-scale targeted sequencing", Nature Biotechnology, 2009, pp. 1025-1031, vol. 27, No. 11, Publisher: Nature Publishing Group.

Trapnell, C., "How to map billions of short reads onto genomes", Nature Biotechnology, 2009, pp. 455-457, vol. 27.

Turner, E.H., et al., "Massively parallel exon capture and library-free resequencing across 16 genomes", Nature Methods, 2009, pp. 315-316, vol. 6, No. 5, Publisher: Nature America, Inc.

Warren, R.L., et al., "Assembling millions of short DNA sequences using SSAKE", Bioinformatics, 2007, pp. 500-501; doi: 10.1093/bioinformatics/btl629, vol. 23, No. 4.

Weese, D., et al., "RazerS-fast read mapping with sensitivity control", Genome Research, 2009, pp. 1646-1654, vol. 19, Publisher: Cold Spring Harbor Laboratory Press.

Wu, T.D., et al., "GMAP a genmic mapping and alignment program for mRNA and EST sequences", Bioinfomatics, 2005, pp. 1859-1875, vol. 21, No. 9.

Wu, T.D., et al., "Fast and SNP-tolerant detection of complex variants and splicing in short reads", Bioinformatics, 2010, pp. 873-881, vol. 26, No. 7, Publisher: Oxford University Press.

Zerbino, D.R., et al., "Velvet: Algorithms for de novo read assembly using de Bruijin graphs", Genome Research, 2008, pp. 821-829, vol. 18, Publisher: Cold Spring Harbor Laboratory Press.

Zhou, X., et al., "CRAG: De novo characterization of cell-free DNA fragmentation hotspots in plasma whole-genome sequencing", bioRxiv, 2020, http://doi.org/10.1101/2020.07.16.201350, 34 pages.

* cited by examiner

FIG. 6
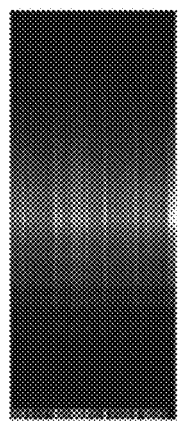 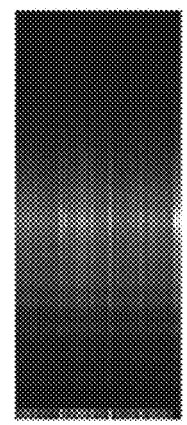 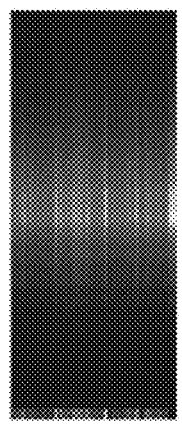
Healthy subjects    Liver cancer patents    Esophageal cancer patents

METHOD FOR DIAGNOSING CANCER AND PREDICTING CANCER TYPE BY USING TERMINAL SEQUENCE MOTIF FREQUENCY AND SIZE OF CELL-FREE NUCLEIC ACID FRAGMENT

CROSS-REFERENCE TO RELATED APPLICATIONS

This is a Continuation under 35 USC § 120 and 35 USC § 365(c) of International Patent Application No. PCT/KR2022/007651 filed May 30, 2022, and claims priority under 35 USC § 119 of Korean Patent Application No. 10-2021-0068891 filed May 28, 2021. The disclosures of all such applications are hereby incorporated herein by reference in their respective entireties, for all purposes.

FIELD OF THE INVENTION

The present invention relates to a method for diagnosing cancer and predicting a cancer type using fragment end motif frequencies and sizes of cell-free nucleic acid, and more preferably, to a method for diagnosing cancer and predicting a cancer type by extracting nucleic acids from a biological sample to obtain sequence information (reads), acquiring end motif frequencies and sizes of nucleic acid fragments based on the aligned reads, converting the end motif frequencies and sizes of nucleic acid fragments into vectorized data, inputting the vectorized data to a trained artificial intelligence model and analyzing a resulting calculated value.

BACKGROUND ART

Cancer diagnosis in clinical practice is usually performed by tissue biopsy after history examination, physical examination, and clinical evaluation. Cancer diagnosis based on clinical trials is possible only when the number of cancer cells is 1 billion or more and the diameter of the cancer is 1 cm or more. In this case, cancer cells already have the potential to metastasize and at least half thereof have already metastasized. In addition, tissue biopsy is invasive, which disadvantageously causes patients considerable discomfort and is often incompatible with cancer therapy. Further, tumor markers for monitoring substances produced directly or indirectly from cancer are used in cancer screening. However, the tumor markers have limited accuracy because more than half of tumor marker screening results indicate normal even in the presence of cancer and tumor marker screening results often indicate positive even in the absence of cancer.

Recently, in response to the requirements for cancer diagnosis methods, such as relative ease, non-invasiveness, high sensitivity and high specificity, liquid biopsy using bodily fluids from patients has been widely used for cancer diagnosis and follow-up examination. Liquid biopsy is a non-invasive diagnostic method that is attracting great attention as an alternative to conventional invasive diagnosis and examination methods.

Recently, a method for diagnosing cancer and determining a cancer type using cell free DNA obtained from liquid biopsy has been developed (U.S. patent Ser. No. 10/975,431, Zhou, Xionghui et al., bioRxiv, 2020.07.16.201350). In particular, a method of analyzing the motif frequency information of the cell-free nucleic acid end sequence and using the information for cancer diagnosis, prenatal diagnosis, or organ transplant monitoring is known (WO 2020-125709, Peiyong Jiang et al., Cancer Discovery, Vol. 10, 2020, pp. 664-673).

Meanwhile, artificial neural networks are computational models implemented in software or hardware that mimic the computational ability of biological systems using a large number of artificial neurons connected via connective lines. Artificial neural networks use artificial neurons, which represent the functions of biological neurons in simplified form. Artificial neural networks conduct human cognition or learning processes by interconnecting the artificial neurons through connective lines having respective connection intensities. The term "connection intensity", which is interchangeable with "connection weight, refers to a predetermined value of the connection line. Artificial neural network learning may be classified into supervised learning and unsupervised learning. Supervised learning is a method of providing input data and output data corresponding thereto to a neural network and updating the connection intensities of connecting lines so that output data corresponding to the input data is output. Representative learning algorithms include delta rule and back propagation learning. Unsupervised learning is a method in which an artificial neural network independently learns connection intensities using only input data, without a target value. Unsupervised learning updates connection weights based on correlations between input patterns.

Applying large amounts of data to machine learning causes the so-called "curse of dimensionality" problem due to the increased complexity and the greater number of dimensions. In other words, as the number of dimensions of the required data approaches infinity, the distance between any two points also approaches infinity, and the amount of data, that is, the density, becomes lower in high-dimensional space, which makes it impossible to properly reflect the features of the data (Richard Bellman, Dynamic Programming, 2003, chapter 1). Recently developed deep learning has a structure in which a hidden layer is present between an input layer and an output layer, and has been reported to greatly improve the performance of the classifier in high-dimensional data such as images, videos, and signal data by processing a linear combination of variable values transmitted from the input layer with nonlinear functions (Hinton, Geoffrey, et al., IEEE Signal Processing Magazine Vol. 29.6, pp. 82-97, 2012).

Various patents (KR 10-2018-124550, KR 10-2019-7038076, KR 10-2019-0003676, and KR 10-2019-0001741) describe the use of artificial neural networks in biological fields, but there is a lack of research on methods for predicting cancer types through artificial neural network analysis based on cell-free DNA (cfDNA) sequencing information in blood.

Accordingly, as a result of extensive and earnest efforts to solve the above problems and develop a method for diagnosing cancer and predicting a cancer type based on artificial intelligence with high sensitivity and accuracy, the present inventors found that cancer diagnosis and cancer type prediction can be realized with high sensitivity and accuracy by generating vectorized data based on information on the end motifs and lengths of cell-free nucleic acid fragments and analyzing the data using a trained artificial intelligence model, and the present invention has been completed based on this finding.

SUMMARY OF THE INVENTION

Therefore, it is one object of the present invention to provide a method for diagnosing cancer and predicting a cancer type using end motif frequencies and sizes of cell-free nucleic acid fragments.

It is another object of the present invention to provide a device for diagnosing cancer and predicting a cancer type using the end motif frequencies and sizes of cell-free nucleic acid fragments.

It is another object of the present invention to provide a computer-readable storage medium including instructions configured to be executed by a processor for diagnosing cancer and predicting a cancer type by the method described above.

In accordance with one aspect of the present invention, provided is a method for providing information for diagnosing cancer and predicting a cancer type, the method including (a) extracting nucleic acids from a biological sample to obtain sequence information, (b) aligning the sequence information (reads) with a reference genome database, (c) acquiring end motif frequencies and sizes of nucleic acid fragments based on the aligned sequence information (reads), (d) generating vectorized data using the motif frequencies and sizes of nucleic acid fragments, (e) inputting the generated vectorized data into a trained artificial intelligence model, analyzing the data, and comparing an analyzed output value with a cut-off value to determine whether or not cancer develops, and (f) predicting a cancer type through comparison of the output value.

In accordance with another aspect of the present invention, provided a method for diagnosing cancer and predicting a cancer type, the method including (a) extracting nucleic acids from a biological sample to obtain sequence information, (b) aligning the sequence information (reads) with a reference genome database, (c) acquiring end motif frequencies and sizes of nucleic acid fragments based on the aligned sequence information (reads), (d) generating vectorized data using the motif frequencies and sizes of nucleic acid fragments, (e) inputting the generated vectorized data into a trained artificial intelligence model, analyzing the data, and comparing an analyzed output value with a cut-off value to determine whether or not cancer develops, and (f) predicting a cancer type through comparison of the output value.

In accordance with another aspect of the present invention, provided is a device for diagnosing cancer and predicting a cancer type, the device including a decoder configured to extract nucleic acids from a biological sample and decode sequence information, an aligner configured to align the decoded sequences with a reference genome database, a nucleic acid fragment analyzer configured to acquire end motif frequencies and sizes of nucleic acid fragments based on the aligned sequences, a data generator configured to generate vectorized data using the end motif frequencies and sizes of nucleic acid fragments, a cancer diagnostic unit configured to input the generated vectorized data into a trained artificial intelligence model, analyze the data, compare a resulting output value with a cut-off value, and thereby determine whether or not cancer develops, and a cancer type predictor configured to analyze the output value and thereby predict the cancer type.

In accordance with another aspect of the present invention, provided is a computer-readable storage medium including an instruction configured to be executed by a processor for diagnosing cancer and predicting a cancer type through the following steps including (a) extracting nucleic acids from a biological sample to obtain sequence information, (b) aligning the sequence information (reads) with a reference genome database, (c) acquiring end motif frequencies and sizes of nucleic acid fragments based on the aligned sequence information (reads), (d) generating vectorized data using the motif frequencies and sizes of nucleic acid fragments, (e) inputting the generated vectorized data to a trained artificial intelligence model, analyzing the data, and comparing an analyzed output value with a cut-off value to determine whether or not cancer develops, and (f) predicting a cancer type through comparison of the output value.

DESCRIPTION OF DRAWINGS

FIG. 6 is an example of visualization of a FEMS table created based on data of healthy subjects, liver cancer patients, and esophageal cancer patients according to an embodiment of the present invention;

DETAILED DESCRIPTION OF THE INVENTION

Figure 1:
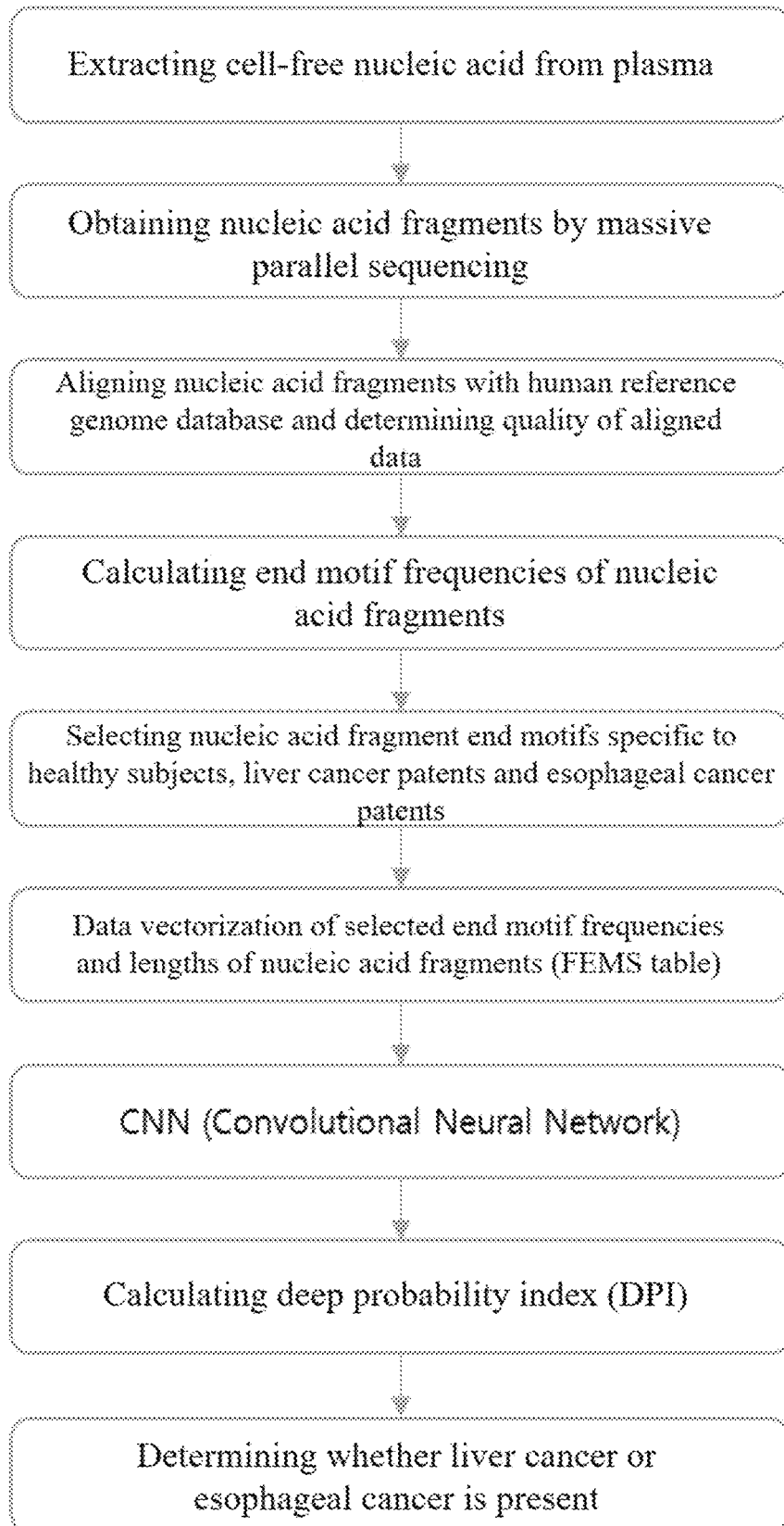
FIG. 1 is an overall flowchart illustrating a method for diagnosing cancer and predicting a cancer type using end motifs and sizes of cell-free nucleic acid fragments according to the present invention.

Unless defined otherwise, all technical and scientific terms used herein have the same meanings as appreciated by those skilled in the field to which the present invention pertains. In general, the nomenclature used herein is well-known in the art and is ordinarily used.

Although terms such as "first", "second", "A", "B", etc. may be used to describe various components, these components are not to be limited by these terms, and the terms are only used to distinguish one component from another component. For instance, a "first" component may be named as a "second" component, and similarly, the "second" component may also be referred to as a "first" component, without departing from the scope of the technology to be described below. The term "and/or" includes a combination of a plurality of related listed items or any of a plurality of related listed items.

In the terms used herein, the singular forms are intended to include plural forms as well, unless the context clearly indicates otherwise, and it will be further understood that the terms such as "comprise", "include", etc. specify the presence of stated features, integers, steps, operations, components, parts, or combinations thereof, but do not preclude the presence or addition of one or more other features, integers, steps, operations, components, parts, or combinations thereof.

Before a detailed description of the drawings, it should be clarified that the classification of the constituent units in the present specification is merely a division depending on the main function that each constituent unit is responsible for. Specifically, two or more constituent units to be described below may be combined into one constituent unit, or one constituent unit may be divided into two or more for each more subdivided function. Furthermore, it will be understood that each of the constituent units to be described below may additionally perform some or all of the functions of other constituent units in addition to the main function it is responsible for and also that some of the main functions that the constituent units are responsible for may be exclusively performed by other constituent units.

Moreover, in performing the method or operation method, individual processes constituting the method may occur differently from the specified order unless a specific order is clearly described in context. Specifically, individual processes may occur in the same order as specified, may be performed substantially simultaneously, or may be performed in reverse order.

It was found in the present invention that cancer diagnosis and cancer type prediction with high sensitivity and accuracy are possible by aligning sequencing data obtained from a sample with a reference genome, acquiring end motif frequencies and sizes of nucleic acid fragments based on the aligned sequence information (reads), generating vectorized data using the motif frequencies and sizes of nucleic acid fragments, and calculating a DPI using a trained artificial intelligence model.

That is, in one embodiment of the present invention, developed is a method including sequencing DNA extracted from blood, aligning the sequencing data with a reference genome, acquiring end motif frequencies and sizes of nucleic acid fragments using the aligned sequence information, generating vectorized data with the end motif frequencies of nucleic acid fragments on the X-axis and the sizes of nucleic acid fragments on the Y-axis, allowing a deep-learning model to perform learning on the data to calculate a DPI, diagnosing cancer through comparison of the DPI with the reference value and then determining a type of cancer showing the highest DPI among the calculated DPIs for respective cancer types as the cancer type of the sample (FIG. 1).

In another aspect, the present invention is directed to a method for providing information for diagnosing cancer and predicting a cancer type, the method including:
(a) extracting nucleic acids from a biological sample to obtain sequence information;
(b) aligning the sequence information (reads) with a reference genome database;
(c) acquiring end motif frequencies and sizes of nucleic acid fragments based on the aligned sequence information (reads);
(d) generating vectorized data using the motif frequencies and sizes of nucleic acid fragments;
(e) inputting the generated vectorized data into a trained artificial intelligence model, analyzing the data, and comparing an analyzed output value with a cut-off value to determine whether or not cancer develops; and
(f) predicting a cancer type through comparison of the output value.

In the present invention, any nucleic acid fragment can be used without limitation, as long as it is a fragment of a nucleic acid extracted from a biological sample, and the nucleic acid fragment is preferably a fragment of cell-free nucleic acid or intracellular nucleic acid, but is not limited thereto.

In the present invention, the nucleic acid fragment may be obtained by any method known to those skilled in the art, preferably direct sequencing, next-generation sequencing, sequencing through non-specific whole genome amplification, or probe-based sequencing, but the method is not limited thereto.

In the present invention, the cancer may be a solid cancer or a blood cancer, is preferably selected from the group consisting of non-Hodgkin lymphoma, non-Hodgkin lymphoma, acute-myeloid leukemia, acute-lymphoid leukemia, multiple myeloma, head and neck cancer, lung cancer, glioblastoma, colorectal/rectal cancer, pancreatic cancer, breast cancer, ovarian cancer, melanoma, prostate cancer, liver cancer, thyroid cancer, stomach cancer, gallbladder cancer, biliary tract cancer, bladder cancer, small intestine cancer, cervical cancer, cancer of unknown primary, kidney cancer, esophageal cancer and mesothelioma, and is more preferably liver cancer or esophageal cancer, but the cancer is not limited thereto.

In the present invention,
step (a) includes:
(a-i) obtaining nucleic acids from a biological sample;
(a-ii) removing proteins, fats, and other residues from the collected nucleic acids using a salting-out method, a column chromatography method, or a bead method to obtain purified nucleic acids;
(a-iii) producing a single-end sequencing or paired-end sequencing library for the purified nucleic acids or nucleic acids randomly fragmented by an enzymatic digestion, pulverization, or hydroshear method;
(a-iv) reacting the produced library with a next-generation sequencer; and
(a-v) obtaining sequence information (reads) of the nucleic acids in the next-generation sequencer.

In the present invention, the obtaining the sequence information in step (a) may be characterized in that the isolated cell-free DNA is obtained through whole-genome sequencing to a depth of 1 million to 100 million reads.

In the present invention, the biological sample is any material, biological fluid, tissue, or cell obtained from or derived from a subject, and examples thereof may include, but are not limited to, whole blood, leukocytes, peripheral blood mononuclear cells, buffy coat, blood (including plasma and serum), sputum, tears, mucus, nasal washes, nasal aspirate, breath, urine, semen, saliva, peritoneal washings, pelvic fluids, cystic fluid, meningeal fluid, amniotic fluid, glandular fluid, pancreatic fluid, lymph fluid, pleural fluid, nipple aspirate, bronchial aspirate, synovial fluid, joint aspirate, organ secretions, cells, cell extract, hair, oral cells, placental cells, cerebrospinal fluid, and mixtures thereof.

In the present invention, the next-generation sequencer may be used for any sequencing method known in the art. Sequencing of nucleic acids isolated using the selection method is typically performed using next-generation sequencing (NGS). Next-generation sequencing includes any sequencing method that determines the nucleotide sequence either of each nucleic acid molecule or of a proxy cloned from each nucleic acid molecule so as to be highly similar thereto (e.g., 105 or more molecules are sequenced simultaneously). In one embodiment, the relative abundance of nucleic acid species in the library can be estimated by counting the relative number of occurrences of the sequence homologous thereto in data produced by sequencing experimentation. Next-generation sequencing is known in the art, and is described, for example, in Metzker, M. (2010), Nature Biotechnology Reviews 11:31-46, which is incorporated herein by reference.

In one embodiment, next-generation sequencing is performed to determine the nucleotide sequence of each nucleic acid molecule (using, for example, a HelioScope Gene-Sequencing system from Helicos Biosciences or a PacBio RS system from Pacific Biosciences). In other embodiments, massive parallel short-read sequencing, which produces more bases of the sequence per sequencing unit than other sequencing methods, for example, other sequencing methods that produce fewer but longer reads, determines the nucleotide sequence of a proxy cloned from each nucleic acid molecule (using, for example, a Solexa sequencer from Illumina Inc., located in San Diego, CA; 454 Life Sciences (Branford, Connecticut) and Ion Torrent). Other methods or devices for next-generation sequencing may be provided by 454 Life Sciences (Branford, Connecticut), Applied Biosystems (Foster City, CA; SOLiD Sequencer), Helicos Biosciences Corporation (Cambridge, MA) and emulsion and microfluidic sequencing nanodrops (e.g., GnuBIO Drops), but are not limited thereto.

Platforms for next-generation sequencing include, but are not limited to, the FLX System genome sequencer (GS) from Roche/454, the Illumina/Solexa genome analyzer (GA), the Support Oligonucleotide Ligation Detection (SOLiD) system from Life/APG, the G.007 system from Polonator, the HelioScope gene-sequencing system from Helicos Biosciences, and the PacBio RS system from Pacific Biosciences.

NGS technologies may, for example, include one or more of template production, sequencing, imaging, and data analysis steps.

Template production. Methods for producing templates include randomly disrupting nucleic acids (e.g., genomic DNA or cDNA) into small sizes and producing sequencing templates (e.g., fragment templates or mate-pair templates). Spatially separated templates may be attached or immobilized on a solid surface or support, which allows simultaneous large-scale sequencing reactions to be performed. Examples of types of templates that can be used for NGS reactions include templates amplified from clones derived from single DNA molecules and single DNA molecule templates.

Methods for producing the templates amplified from clones include, for example, emulsion PCR (emPCR) and solid-phase amplification.

EmPCR may be used to produce templates for NGS. Typically, a library of nucleic acid fragments is produced, and adapters containing universal priming sites are ligated to the ends of the fragments. The fragments are then denatured into single strands and captured using beads. Each bead captures a single nucleic acid molecule. After amplification and enrichment of emPCR beads, a large amount of templates can be attached, immobilized to a polyacrylamide gel on a standard microscope slide (from, for example, Polonator) and chemically crosslinked to an amino-coated glass surface (e.g., Life/APG; Polonator), or deposited in individual PicoTiterPlate (PTP) wells (e.g., Roche/454). At this time, an NGS reaction may be performed.

Solid-phase amplification can also be used to produce templates for NGS. Typically, the front and rear primers are covalently attached to the solid support. The surface density of the amplified fragment is defined as the ratio of primer to template on the support. Solid-phase amplification is capable of producing millions of spatially separated template clusters (e.g., Illumina/Solexa). The ends of the template cluster can be hybridized to universal primers for NGS reactions.

Other methods for producing clone-amplified templates include, for example, multiple displacement amplification (MDA) (Lasken R. S.; Curr. Opin. Microbiol. 2007; 10(5): 510-6). MDA is a non-PCR-based DNA amplification method. The reaction involves annealing random hexamer primers to templates and synthesizing DNA using a high-fidelity enzyme, typically Φ29, at a constant temperature. MDA can yield large-scale products with a lower error frequency.

Template amplification methods such as PCR can bind the NGS platform to the target or enrich specific regions of the genome (e.g., exons). Representative template enrichment methods include, for example, microdroplet PCR (Tewhey R. et al., Nature Biotech. 2009, 27:1025-1031), custom-designed oligonucleotide microarrays (e.g., Roche/Nimble-Gen oligonucleotide microarrays), solution-based hybridization (e.g., molecular inversion probes, MIPs) (Porreca G J et al., Nature Methods, 2007, 4:931-936; Krishnakumar S. et al., Proc. Natl. Acad. Sci. USA, 2008, 105:9296-9310; Turner E H et al., Nature Methods, 2009, 6:315-316), and biotinylated RNA capture sequences (Gnirke A. et al., Nat. Biotechnol. 2009; 27(2):182-9).

Single-molecule templates are another type of template that can be used for NGS reactions. Spatially separated single-molecule templates may be immobilized on a solid support by a variety of methods. In one approach, each primer molecule is covalently attached to a solid support. The adapter is added to the template and the template is then hybridized to the immobilized primer. In another approach, a single-molecule template is covalently attached to a solid support by priming and extending a single-stranded single-molecule template from the immobilized primer. The universal primer is then hybridized to the template. In another approach, a single polymerase molecule is attached to a solid support to which a primed template is bound.

Sequencing and imaging. Representative sequencing and imaging methods for NGS include, but are not limited to, cyclic reversible termination (CRT), sequencing by ligation (SBL), pyrosequencing, and real-time sequencing.

CRT uses reversible terminators in a cyclic method that includes, at a minimum, steps of nucleotide incorporation, fluorescence imaging, and cleavage. Typically, a DNA polymerase incorporates a single fluorescently modified nucleotide complementary to the nucleotide of the template base in the primer. DNA synthesis is terminated after incorporation of a single nucleotide, and the unincorporated nucleotides are washed out. Imaging is performed to determine the homology of the incorporated labeled nucleotides. Then, in the cleavage step, the terminator/inhibitor and the fluorescent dye are removed. Representative NGS platforms using the CRT method include, but are not limited to, Illumina/Solexa Genome Analyzer (GA), which uses a clone-amplification template method combined with a 4-color CRT method involving detection using total internal reflection fluorescence (TIRF); and Helicos Biosciences/HelioScope, using a single-molecule template method combined with a 1-color CRT method involving detection using TIRF.

SBL uses a DNA ligase and either a 1-base-encoded probe or a 2-base-encoded probe for sequencing.

Typically, a fluorescently labeled probe is hybridized to a complementary sequence adjacent to the primed template. DNA ligases are used to ligate dye-labeled probes to primers. After the non-ligated probes are washed, fluorescence imaging is performed to determine the identity of the ligated probes. The fluorescent dye may be removed using a cleavable probe that regenerates the 5'-PO4 group for subsequent ligation cycles. Alternatively, new primers may be hybridized to the template after old primers have been removed. Representative SBL platforms include, but are not limited to, Life/APG/SOLiD (support oligonucleotide ligation detection), which uses a two-base-encoded probe.

The pyrosequencing method is based on detection of activity of DNA polymerase with another chemiluminescent enzyme. Typically, this method includes sequencing a single strand of DNA by synthesizing complementary strands of one base pair at a time and detecting the base that is actually added in each step. The template DNA is stationary, and solutions of A, C, G, and T nucleotides are sequentially added and removed during the reaction. Light is generated only when the nucleotide solution replenishes the unpaired base of the template. The sequence of the solution generating the chemiluminescent signal is used to determine the sequence of the template. Representative pyrosequencing platforms include, but are not limited to, those from Roche/454, using DNA templates produced from 1 to 2 million beads deposited in PTP wells by emPCR.

Real-time sequencing involves imaging the continuous incorporation of dye-labeled nucleotides during DNA synthesis. Representative real-time sequencing platforms include, but are not limited to, a platform from Pacific Biosciences, which uses DNA polymerase molecules attached to the surface of respective zero-mode waveguide (ZMW) detectors to obtain sequence information when phosphate-linked nucleotides are incorporated in the growing primer strands; the Life/VisiGen platform using genetically engineered DNA polymerases along with attached fluorescent dyes to create an enhanced signal after incorporation of the nucleotide by fluorescence resonance energy transfer (FRET); and a platform from LI-COR Biosciences using dye-quencher nucleotides in sequencing reactions.

Other NGS methods include, but are not limited to, nanopore sequencing, sequencing by hybridization, nanotransistor-array-based sequencing, Polony sequencing, scanning tunneling microscopy (STM)-based sequencing, and nanowire molecular sensor-based sequencing.

Nanopore sequencing involves electrophoresis of nucleic acid molecules in solution through nano-scale pores that provide a highly airtight area for analysis of single-nucleic-acid polymers. Representative nanopore sequencing methods are described in Branton D. et al., Nat. Biotechnol. 2008; 26(10):1146-53] and elsewhere.

Sequencing by hybridization is a non-enzymatic method using DNA microarrays. Typically, a single pool of DNA is fluorescently labeled and hybridized into an array containing a known sequence. The hybridization signal from a given spot on the array can be used to identify the DNA sequence. Binding of one strand of DNA to another strand complementary thereto in a DNA double strand is sensitive even to single-base mismatches when the hybrid region is short or when a specified mismatch detection protein is present. Representative hybridization sequencing methods are described, for example, in Hanna G. J. et al., J. Clin. Microbiol. 2000; 38(7): 2715-21; and Edwards J. R. et al., Mut. Res. 2005; 573(1-2): 3-12.

Polony sequencing is based on Polony amplification and multiple single-base-extension (FISSEQ). Polony amplification is a method of amplifying DNA in situ on a polyacrylamide film. Representative Polony sequencing methods are described, for example, in US Patent Application Publication No. 2007/0087362.

Nanotransistor-array-based devices such as carbon nanotube field effect transistors (CNTFETs) can also be used for NGS. For example, DNA molecules are extended and driven across nanotubes by microfabricated electrodes. DNA molecules sequentially contact the carbon nanotube surface, and a difference in current flow from the respective bases is created due to charge transfer between the DNA molecule and the nanotube. DNA is sequenced by recording the difference. Representative nanotransistor-array-based sequencing methods are described, for example, in US Patent Publication No. 2006/0246497.

Scanning tunneling microscopy (STM) can also be used for NGS. Using a piezoelectrically controlled probe that performs a raster scan of the specimen, STM forms an image on the surface thereof. STM can be used to image the physical properties of single DNA molecules, causing coherent electron tunneling imaging and spectroscopy, for example, by integrating a flexible actuator-driven gap with a scanning tunneling microscope. Representative sequencing methods using STM are described, for example, in US Patent Application Publication No. 2007/0194225.

Molecular analysis devices consisting of nanowire-molecular sensors can also be used for NGS. Such devices can detect the interaction of nitrogenous substances disposed on nucleic acid molecules and nanowires such as DNA. Molecular guides are disposed to guide molecules near the molecular sensors to allow interaction and subsequent detection. Representative sequencing methods using nanowire molecular sensors are described, for example, in US Patent Application Publication No. 2006/0275779.

Double-stranded sequencing may be used for NGS. Double-stranded sequencing uses blocking and unblocking primers to sequence both the sense and antisense strands of DNA. Typically, this method includes: annealing an unblocking primer to a first strand of a nucleic acid; annealing a second blocking primer to a second strand of the nucleic acid; extending the nucleic acid along the first strand with a polymerase; terminating the first sequencing primer; deblocking the second primer; and extending the nucleic acid along the second strand. Representative double-stranded sequencing methods are described, for example, in U.S. Pat. No. 7,244,567.

After NGS reads are formed, they are aligned or de novo assembled to a known reference sequence.

For example, identification of genetic modifications such as single-nucleotide polymorphisms and structural variants in a sample (e.g., a tumor sample) can be performed by aligning NGS reads to a reference sequence (e.g., a wild-type sequence). A method of aligning NGS reads to sequences is described, for example, in Trapnell C. and Salzberg S. L. Nature Biotech., 2009, 27:455-457.

Examples of de novo assembly are described, for example, in Warren R. et al., Bioinformatics, 2007, 23:500-501; Butler J. et al., Genome Res., 2008, 18:810-820; and Zerbino D. R. and Birney E., Genome Res., 2008, 18:821-829.

Sequence alignment or assembly can be performed using read data from one or more NGS platforms, for example, by mixing Roche/454 and Illumina/Solexa read data. In the present invention, the alignment may be performed using the BWA algorithm and the hg19 sequence, but is not limited thereto.

In the present invention, the sequence alignment of step (b) includes a computational method or approach using a computer algorithm to determine the case where there is the possibility that a sequence (e.g., a short-read sequence obtained, for example, through next-generation sequencing) is derived from the genome or the case where there is identity therebetween by evaluating the similarity between a read sequence and a reference sequence. Various algorithms may be applied to the sequence alignment problem. Some algorithms are relatively slow, but enable relatively high specificity. These include, for example, dynamic-programming-based algorithms. Dynamic programming is a method of solving complicated problems by segmenting them into simpler steps. Other approaches are more efficient, but are typically not exhaustive, and include, for example, heuristic algorithms and probabilistic methods designed for massive database searches.

Typically, the alignment process may include two steps, namely candidate screening and sequence alignment. Candidate screening reduces the search space for sequence alignments from the entire genome in order to obtain a shorter list of possible alignment positions. As the term literally implies, sequence alignment includes aligning sequences including the sequences obtained during candidate screening. This may be performed using broad alignment (e.g., Needleman-Wunsch alignment) or local alignment (e.g., Smith-Waterman alignment).

Most attribute sorting algorithms may have one of three types based on the indexing method: algorithms based on hash tables (e.g. BLAST, ELAND, SOAP), suffix trees (e.g. Bowtie, BWA), and merge sort (for example, slider). Short read sequences are typically used for alignment. Examples of sequence alignment algorithms/programs for short-read sequences include, but are not limited to, BFAST (Homer N. et al., PLoS One. 2009; 4(11):e7767), BLASTN (from blast.ncbi.nlm.nih.gov on the world wide web), BLAT (Kent W. J. Genome Res. 2002; 12(4):656-64), Bowtie (Langmead B. et al., Genome Biol. 2009; 10(3):R25), BWA (Li H. and Durbin R., Bioinformatics, 2009, 25:1754-60), BWA-SW (Li H. and Durbin R., Bioinformatics, 2010; 26(5):589-95), CloudBurst (Schatz M. C., Bioinformatics, 2009; 25(11): 1363-9), Corona Lite (Applied Biosystems, Carlsbad, California, USA), CASHX (Fahlgren N. et al., RNA, 2009; 15, 992-1002), CUDA-EC (Shi H. et al., J. Comput. Biol. 2010; 17(4):603-15), ELAND (bioit.dbi.udel.edu/howto/eland on the world wide web), GNUMAP (Clement N. L. et al., Bioinformatics. 2010; 26(1):38-45), GMAP (Wu T. D. and Watanabe C. K., Bioinformatics, 2005; 21(9):1859-75), GSNAP (Wu T. D. and Nacu S., Bioinformatics, 2010; 26(7):873-81), Geneious Assembler (Biomatters Ltd., Oakland, New Zealand), LAST, MAQ (Li H. et al., Genome Res. 2008; 18(11):1851-8), Mega-BLAST (at ncbi.nlm.nih.gov/blast/megablast.shtml on the world wide web), MOM (Eaves H. L. and Gao Y. Bioinformatics. 2009; 25(7):969-70), MOSAIK (at bioinformatics.bc.edu/marthlab/Mosaik on the world wide web), NovoAlign (at novocraft.com/main/index.php on the world wide web), ALMapper (at fml.tuebingen.mpg.de/raetsch/suppl/palmapper on the world wide web), PASS (Campagna D. et al., Bioinformatics, 2009; 25(7):967-8), PatMaN (Prufer K. et al., Bioinformatics, 2008; 24(13):1530-1), PerM (Chen Y. et al., Bioinformatics, 2009, 25 (19): 2514-2521), ProbeMatch (Kim Y. J. et al., Bioinformatics. 2009; 25(11):1424-5), QPalma (de Bona F. et al., Bioinformatics, 2008, 24(16): i174), RazerS (Weese D. et al., Genome Research, 2009, 19:1646-1654), RMAP (Smith A. D. et al., Bioinformatics, 2009; 25(21): 2841-2), SeqMap (Jiang H. et al., Bioinformatics, 2008; 24:2395-2396), Shrec (Salmela L., Bioinformatics, 2010; 26(10):1284-90), SHRiMP (Rumble S. M. et al., PLoS Comput. Biol., 2009, 5(5):e1000386), SLIDER (Malhis N. et al., Bioinformatics, 2009, 25 (1): 6-13), SLIM Search (Muller T. et al., Bioinformatics, 2001; 17 Suppl 1:S182-9), SOAP (Li R. et al., Bioinformatics, 2008; 24(5):713-4), SOAP2 (Li R. et al., Bioinformatics, 2009; 25(15):1966-7), SOCS (Ondov B. D. et al., Bioinformatics, 2008; 24(23): 2776-7), SSAHA (Ning Z. et al., Genome Res. 2001; 11(10): 1725-9), SSAHA2 (Ning Z. et al., Genome Res. 2001; 11(10):1725-9), Stampy (Lunter G. and Goodson M., Genome Res. 2010, epub ahead of print), Taipan (at taipan.sourceforge.net on the world wide web), UGENE (at ugene.unipro.ru on the world wide web), XpressAlign (at bcgsc.ca/platform/bioinfo/software/XpressAlign on the world wide web), and ZOOM (Bioinformatics Solutions Inc., Waterloo, Ontario, Canada).

A sequence alignment algorithm may be selected based on a number of factors including, for example, the sequencing technique, length of reads, number of reads, available computing resources, and sensitivity/scoring requirements. Different sequence alignment algorithms can achieve different levels of speed, alignment sensitivity, and alignment specificity. Alignment specificity refers to the percentage of target sequence residues that are correctly aligned compared to predicted alignment, as typically shown in the submission. Alignment sensitivity also refers to the percentage of target sequence residues that are aligned, as shown in typically predicted alignments in the submission.

Alignment algorithms such as ELAND or SOAP can be used to align short reads (e.g., from Illumina/Solexa sequencers) to a reference genome when the speed is the first factor to be considered. Alignment algorithms such as BLAST or Mega-BLAST are used to determine similarity using shorter reads (e.g., Roche FLX) when specificity is considered the most important factor, although these methods are slower. Alignment algorithms such as MAQ or NovoAlign can be used for single- or paired-end data when the quality score is important and accuracy is thus essential (e.g. in fast massive SNP searches). Alignment algorithms such as Bowtie or BWA use the Burrows-Wheeler Transform (BWT) and thus require a relatively small memory footprint. Alignment algorithms such as BFAST, PerM, SHRiMP, SOCS, or ZOOM map color space reads and thus can be used along with the SOLiD platform from ABI. In some applications, results from two or more sorting algorithms may be combined.

In the present invention, the length of the sequence information (reads) in step (b) is 5 to 5,000 bp, and the number of sequence information (reads) that are used may be 5,000 to 5 million, but the present invention is not limited thereto.

In the present invention, the end motif of nucleic acid fragment in step (c) may be a sequence pattern of 2 to 30 bases at both ends of the nucleic acid fragment.

That is, with respect to a nucleic acid fragment sequenced by paired-end sequencing as shown below, the end motifs of the nucleic acid fragment are "TACA" sequentially read from the 5' end of the forward strand and "ATTC" sequentially read from the 5' end of the reverse strand.

Forward strand:
(SEQ ID NO: 1)
5'-TACAGACTTTGGAAT-3'

Reverse strand:
(SEQ ID NO: 2)
3'-ATGACTGAAACCTTA-5

In the present invention, the frequency of the end motifs of the nucleic acid fragment in step (c) may be correspond to the number of motifs detected in all the nucleic acid fragments.

That is, when the end motif of the nucleic acid fragment is analyzed based on the four bases at both ends (4-mer motif), a combination of the four bases, namely, A, T, G, and C, located at the $1^{st}$, $2^{nd}$, $3^{rd}$, and $4^{th}$ positions, respectively, is possible and thus motif values of a total of 256 (4*4*4*4) are analyzed.

The count of the number of motifs observed in the entire nucleic acid fragments produced by sequencing is referred to as "motif frequency" and the value calculated by dividing the motif frequency by the total number of nucleic acid fragments produced is referred to "relative frequency".

TABLE 1

| | AAAA | AAAC | AAAG | AAAT |
|---|---|---|---|---|
| Forward Strand | 62,639 | 105,142 | 127,299 | 75,485 |
| Reverse Strand | 62,432 | 105,719 | 126,493 | 75,788 |
| Merged | 125,071 | 210,861 | 253,792 | 151,273 |
| End Motif Relative Freq | 0.00099 | 0.00167 | 0.00201 | 0.00120 |

| | AACA | AACC | ... | TTTT | Row Sum |
|---|---|---|---|---|---|
| Forward Strand | 399,505 | 42,583 | ... | 269,530 | 63,319,687 |
| Reverse Strand | 400,900 | 42,467 | ... | 269,802 | 63,110,437 |
| Merged | 800,405 | 85,050 | ... | 539,332 | 126,430,124 |
| End Motif Relative Freq | 0.00633 | 0.00067 | ... | 0.00427 | — |

As shown in Table 1 above, the total number of nucleic acid fragments is 126,430,124, the number of nucleic acid fragments analyzed from "AAAA", the end motif of the nucleic acid fragments is 125,071, the frequency of the end motif of the nucleic acid fragment, "AAAA", is 125,071, and the relative frequency of end motifs of the nucleic acid fragments calculated by dividing the frequency by the total number of nucleic acid fragments is 0.00099.

In the present invention, the size of the nucleic acid fragment in step (c) may correspond to the number of bases from the 5' end to the 3' end of the nucleic acid fragment.

For example, the size of the nucleic acid fragment analyzed from SEQ ID NOs: 1 and 2 is 15.

In the present invention, the size of the nucleic acid fragment may be 1 to 10,000, preferably 10 to 1,000, more preferably 50 to 500, and most preferably 90 to 250, but the present invention is not limited thereto.

In the present invention, the vectorized data in step (d) may be expressed by the type of the end motif of the nucleic acid fragment plotted on the X-axis and the size of the nucleic acid fragment plotted on the Y-axis.

That is, assuming that there is one nucleic acid fragment as follows,

Forward strand:
(SEQ ID NO: 3)
5'-TACAGACTAGT . . . TTGGAAT-3'

Reverse strand:
(SEQ ID NO: 4)
3'-ATGACTGATCA . . . AACCTTA-5'

Figure 4:
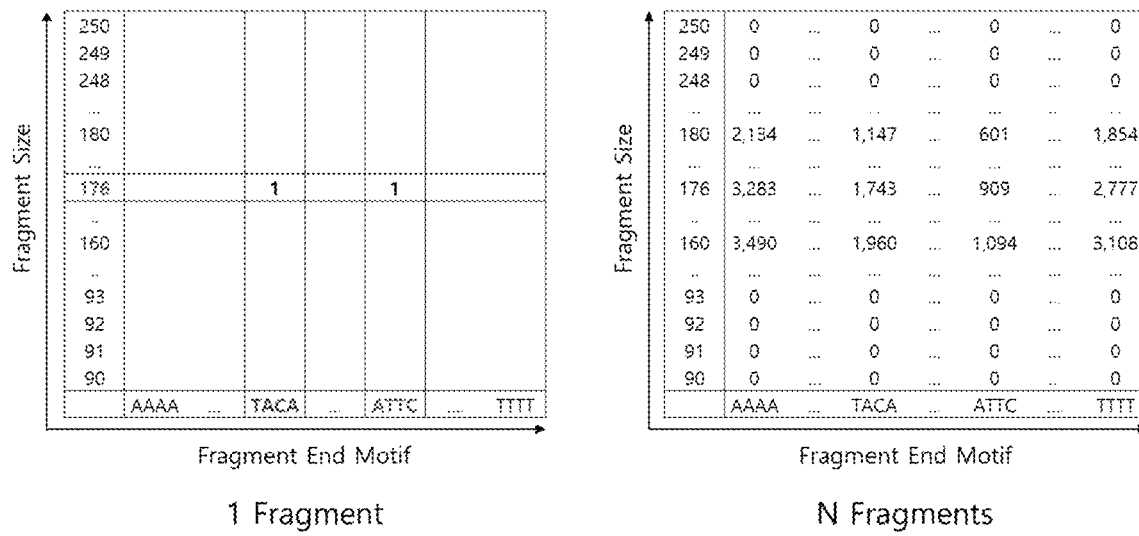
FIG. 4 illustrates an example in which an FEMS table is created from one nucleic acid fragment according to an embodiment of the present invention (left panel) and an example in which the FEMS table is created from all nucleic acid fragments.

Fragment Size: 176 this nucleic acid fragment can be expressed as a two-dimensional vector as shown in the left panel of FIG. 4 and a two-dimensional vector as shown in the right panel of FIG. 4 is generated when this process is performed on an extended entire nucleic acid fragment and accumulated.

In the present invention, the vectorized data may further include the sum of the frequencies for end motifs of nucleic acid fragments and the sum of the frequencies for sizes of nucleic acid fragments.

Figure 5:
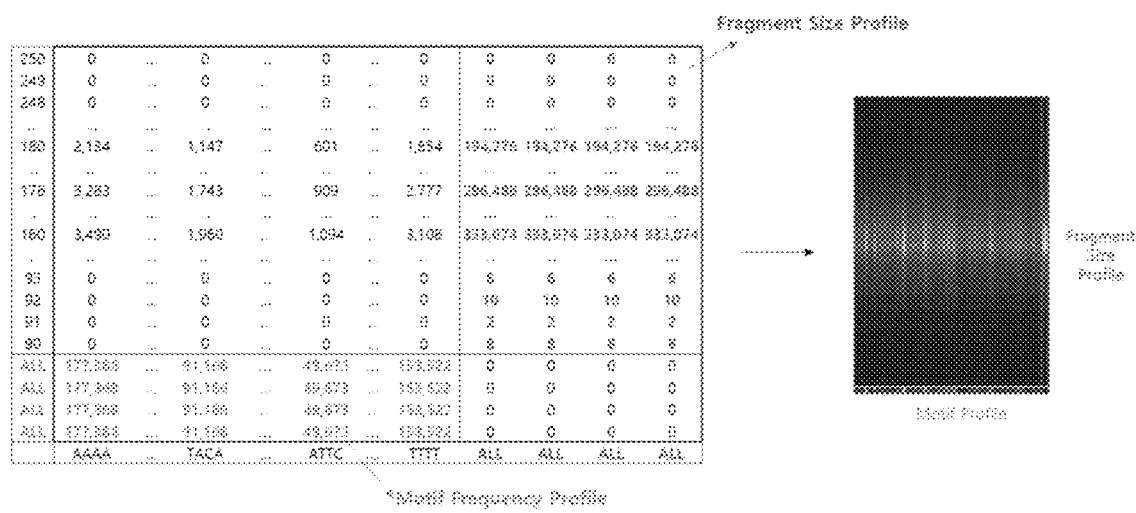
FIG. 5 illustrates an example of a FEMS table created by further performing edge summary according to an embodiment of the present invention (left panel) and a result of visualization thereof (right panel)

That is, the two-dimensional vector as shown in the left panel of FIG. 5 is generated by further performing an edge summary by adding a column sum four times to the bottom of the two-dimensional vector in FIG. 4 in order to add frequency information for each fragment end motif irrelevant to the fragment size, and adding a row sum four times to the rightmost part of the two-dimensional vector of FIG. 4 in order to add the fragment size information irrelevant to the fragment end motif.

In the present invention, the two-dimensional vector is defined as a fragment end motif frequency and size (FEMS) table. The FEMS table is visualized and the result is shown in the right panel of FIG. 5 and FIG. 6.

In the present invention, the vectorized data is preferably an image, but is not limited thereto. An image is basically composed of pixels. If an image composed of pixels is vectorized, it may be expressed as a monochromatic 2D vector (black and white), a three-channel 2D vector (RGB colors), or a four-channel 2D vector (CMYK colors) depending on the type of image.

The vectorized data of the present invention is not limited to image data, and, for example, may be input data of an artificial intelligence model using an n-channel 2D vector (multi-channel vector) created by stacking n black-and-white images.

In the present invention, the method may further include, prior to step (c), separating nucleic acid fragments satisfying a mapping quality score from the aligned nucleic acid fragments.

In the present invention, the mapping quality score may vary depending on a desired criterion, but is preferably 15 to 70, more preferably 50 to 70, and most preferably 60.

In the present invention, any model may be used as the artificial intelligence model in step (e) without limitation, as long as it can be trained to distinguish between images of cancer types and the artificial intelligence model is preferably a deep-learning model.

In the present invention, the artificial intelligence model may be any artificial neural network algorithm capable of analyzing vectorized data based on an artificial neural network without limitation and is preferably selected from the group consisting of a convolutional neural network (CNN), a deep neural network (DNN), and a recurrent neural network (RNN), but is not limited thereto.

In the present invention, the recurrent neural network is selected from the group consisting of a long-short term memory (LSTM) neural network, a gated recurrent unit (GRU) neural network, a vanilla recurrent neural network, and an attentive recurrent neural network.

In the present invention, when the artificial intelligence model is a CNN, the loss function for performing binary classification is represented by Equation 1 below, and the loss function for performing multi-class classification is represented by Equation 2 below.

Equation 1: Binary classification $$\text{loss}(\text{model}(x), y) = -\frac{1}{n}\left[\sum_{i=1}^{n}(y_i \log(model(x_i)) + (1-y_y)\log(1-\text{model}(x_t)))\right]$$

Model $(x_i)$=Artificial intelligence model output in response to $i^{th}$ input
y=Actual label value
n=Number of input data Equation 2: Multi-class classification $$\text{loss}(\text{model}(x), y) = -\frac{1}{n}\sum_{i=1}^{n}\left(\sum_{j=1}^{c}(y_{ij}\log(\text{model}(x_i))_j\right)$$

Model $(x_i)_j = j^{th}$ artificial intelligence model output in response to $i^{th}$ input
y=Actual label value
n=Number of input data
c=Number of classes In the present invention, the binary classification means that the artificial intelligence model learns to determine whether or not cancer develops, and multi-class classification means that the artificial intelligence model learns to distinguish between two or more cancer types.

In the present invention, when the artificial intelligence model is a CNN, learning includes the following steps:
i) classifying the generated vector data into training, validation, and test data,
wherein the training data is used when the CNN model is trained, the validation data is used for hyper-parameter tuning validation, and the test data is used for the test after optimal model production; and
ii) constructing an optimal CNN model through hyper-parameter tuning and training; and
iii) comparing the performance of multiple models obtained through hyper-parameter tuning using validation data and determining the model having the best validation data to be the optimal model.

In the present invention, hyper-parameter tuning is a process of optimizing the values of various parameters (the number of convolution layers, the number of dense layers, the number of convolution filters, etc.) constituting the CNN model. The hyper-parameter tuning is performed using Bayesian optimization and grid search methods.

In the present invention, the internal parameters (weights) of the CNN model are optimized using predetermined hyper-parameters, and it is determined that the model is over-fit when validation loss starts to increase compared to training loss and then training is stopped.

In the present invention, any value resulting from analysis of the input vectorized data by the artificial intelligence model in step (e) may be used without limitation, as long as it is a specific score or real number, and the value is preferably a deep probability index (DPI), but is not limited thereto.

As used herein, the term "deep probability index" refers to a value expressed as a probability value by adjusting the output of artificial intelligence to a scale of 0 to 1 using for the last layer of the artificial intelligence model, a sigmoid function in the case of binary classification and a softmax function in the case of multi-class classification.

In binary classification, training is performed using the sigmoid function such that the DPI is adjusted to 1, provided that cancer develops. For example, when a breast cancer sample and a normal sample are input, training is performed such that the DPI of the breast cancer sample is close to 1.

In multi-class classification, as many DPIs as the number of classes are extracted using the softmax function. The sum of the DPIs is adjusted to 1 and training is performed such that the DPI of the cancer type is actually adjusted to 1. For example, provided that there are three classes, namely, breast cancer, liver cancer, and normal group, when a breast cancer sample is input, training is performed to adjust a DPI of the breast cancer class to about 1.

In the present invention, the resulting output value of step (e) is obtained for each cancer type.

In the present invention, the artificial intelligence model is trained to adjust an output value to about 1 if there is cancer and to adjust an output value to about 0 if there is no cancer. Therefore, performance (training, validation, test accuracy) is measured based on a cut-off value of 0.5. In other words, if the output value is 0.5 or more, it is determined that there is cancer, and if it is less than 0.5, it is determined that there is no cancer.

Here, it will be apparent to those skilled in the art that the cut-off value of 0.5 may be arbitrarily changed. For example, in an attempt to reduce false positives, the cut-off value may be set to be higher than 0.5 as a stricter criterion for determining whether or not there is cancer, and in an attempt to reduce false negatives, the cut-off value may be set to be lower than 0.5 as a weaker criterion for determining that there is cancer.

Most preferably, the cut-off value can be set by determining the probability of the DPI by applying unseen data (data containing a solution that is different from that trained during training) using the trained artificial intelligence model.

In the present invention, (f) predicting a cancer type through comparison of the output result includes determining the cancer type showing the highest value among the output result values as the cancer of the sample.

In another aspect, the present invention is directed to a device for diagnosing cancer and predicting a cancer type, the device including a decoder configured to extract nucleic acids from a biological sample and decode sequence information, an aligner configured to align the decoded sequence with a reference genome database, a nucleic acid fragment analyzer configured to acquire end motif frequencies and sizes of nucleic acid fragments based on the sequence, a data generator configured to generate vectorized data using the end motif frequencies and sizes of nucleic acid fragments, a cancer diagnostic unit configured to input the generated vectorized data to a trained artificial intelligence model, analyze the data, compare the resulting value with a cut-off value, and thereby determine whether or not cancer develops, and a cancer type predictor configured to analyze the output value and thereby predict the cancer type.

In the present invention, the decoding unit may include a nucleic acid injector configured to inject nucleic acids extracted by an independent device and a sequence information analyzer configured to analyze sequence information of the injected nucleic acids, and is preferably an NGS analysis device, but is not limited thereto.

In the present invention, the decoding unit may be configured to receive and decode sequence information data generated by an independent device.

In another aspect, the present invention is directed to a computer-readable storage medium including an instruction configured to be executed by a processor for diagnosing cancer and predicting a cancer type through the following steps including (a) extracting nucleic acids from a biological sample to obtain sequence information, (b) aligning the sequence information (reads) with a reference genome database, (c) acquiring end motif frequencies and sizes of nucleic acid fragments based on the aligned sequence information (reads), (d) generating vectorized data using the motif frequency and size of nucleic acid fragments, (e) inputting the generated vectorized data to a trained artificial intelligence model, analyzing the data, and comparing an analyzed output value with a cut-off value to determine whether or not cancer develops, and (f) predicting a cancer type through comparison of the output value.

The method according to the present disclosure may be implemented using a computer. In one embodiment, the computer includes one or more processors coupled to a chipset. In addition, a memory, storage device, keyboard, graphics adapter, pointing device, and network adapter are connected to the chipset. In one embodiment, performance of the chipset is enabled by a memory controller Hub and an I/O controller hub. In other embodiments, the memory may be used by being directly connected to the processor instead of the chipset. The storage device is any device capable of holding data, including a hard drive, CD-ROM (compact disc read-only memory), DVD, or other memory devices. The memory is associated with data and instructions used by the processor. The pointing device may be a mouse, track ball, or another type of pointing device, and is used in combination with a keyboard to transmit input data to a computer system. The graphics adapter presents images and other information on the display. The network adapter is connected to the computer system through a local-area or long-distance communication network. The computer used herein is not limited to the above configuration, but may not include some configuration or may include an additional configuration, and may also be a part of a storage area network (SAN), and the computer of the present disclosure may be configured to be adapted to the execution of a module in a program for implementing the method according to the present invention.

As used herein, the module may be a functional and structural combination of hardware for performing the technical idea according to the present disclosure and software for driving the hardware. For example, the module may indicate a logical unit of a predetermined code and a hardware resource for executing the predetermined code, and does not necessarily mean a physically connected code or one type of hardware, as will be apparent to those skilled in the art.

In another aspect, the present invention is directed a method for diagnosing cancer and predicting a cancer type, the method including (a) extracting nucleic acids from a biological sample to obtain sequence information, (b) aligning the sequence information (reads) with a reference genome database, (c) acquiring end motif frequencies and sizes of nucleic acid fragments based on the aligned sequence information (reads), (d) generating vectorized data using the motif frequencies and sizes of nucleic acid fragments, (e) inputting the generated vectorized data into a trained artificial intelligence model, analyzing the data, and comparing an analyzed output value with a cut-off value to determine whether or not cancer develops, and (f) predicting a cancer type through comparison of the output value.

EXAMPLE

Hereinafter, the present invention will be described in more detail with reference to examples. However, it will be obvious to those skilled in the art that these examples are provided only for illustration of the present invention, and should not be construed as limiting the scope of the present invention.

Example 1. Extracting DNA from Blood to Perform Next-Generation Sequencing 10 mL of blood was collected from each of 349 normal subjects, 51 liver cancer patients, and 108 esophageal cancer patients, and stored in an EDTA tube. Within 2 hours after blood collection, only the plasma was primarily centrifuged at 1,200 g and 4° C. for 15 minutes, and then the primarily centrifuged plasma was secondarily centrifuged at 16,000 g and 4° C. for 10 minutes to isolate the plasma supernatant excluding the precipitate. Cell-free DNA was extracted from the isolated plasma using a Tiangenmicro DNA kit (Tiangen), a library preparation process was performed using a MGIEasy cell-free DNA library prep set kit, and then sequencing was performed in a 100 base paired end mode using a DNBseq G400 device (MGI). As a result, about 170 million reads were found to be produced from each sample.

Example 2. Selection of Nucleic Acid Fragment End Motif and Nucleic Acid Fragment Size 2-1. Selection of Nucleic Acid Fragment End Motif The nucleic acid fragment end motifs were determined from 4 bases (A, T, G, C), and among a total of 256 (4*4*4*4) motifs, some motifs had no relative frequency difference between normal, HCC and EC groups. A FEMS table generated including a motif not having such a difference may act as noise that only increases the amount of computation of the model without providing information essential for classification. Therefore, in order to exclude these meaningless motifs, only specific motifs having significant relative frequency differences between the three groups were selected.

In addition, in order to prevent the model overfitting issue in the size and motif selection process, only the training set was used in the size and motif selection process.

Figure 2:
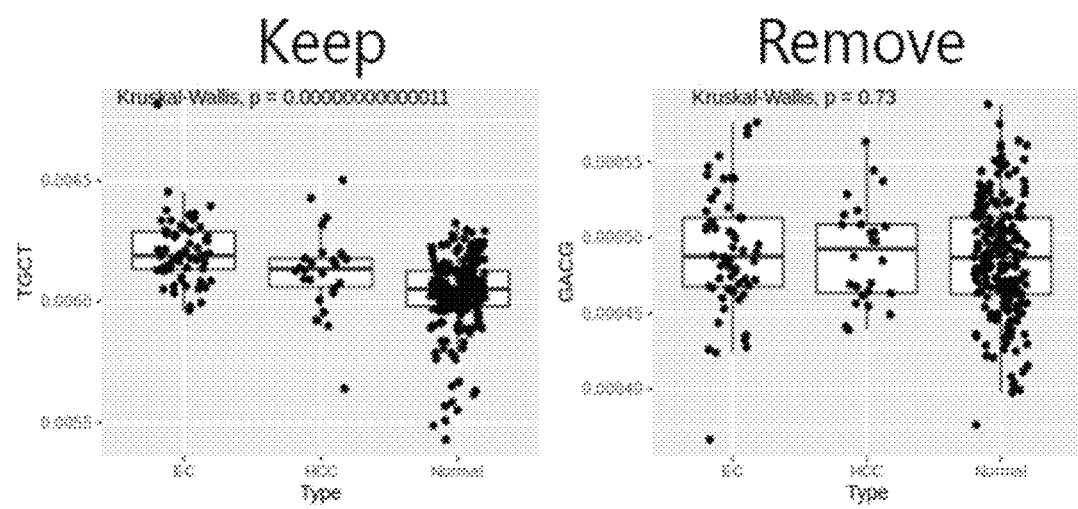
FIG. 2 is an example of a process of selecting motifs having a difference in expression frequency between healthy subjects and cancer patients, or between respective cancer types according to an embodiment of the present invention.

That is, the nucleic acid fragment end motifs were set with 4 bases (A, T, G, C) using the NGS data generated in Example 1 and some motifs that had statistically significant (Kruskal-Wallis Test, FDR-adjust $p<0.05$) relative frequency difference between healthy subjects (Normal), hepatocellular carcinoma (HCC), and esophageal cancer (EC) patient groups were selected from a total of 256 types (4*4*4*4) of motifs (FIG. 2).

In addition, motifs having an average frequency higher than the random baseline (1/256, 0.004) in the healthy subject group were further selected from the motifs selected through the above process in order to prevent overfitting.

As a result, a total of 84 motifs were obtained and detailed motif information is as follows:

```
CTGG, ACTT, CCTA, TGGA, TGGG, CAGG, TATA, CCTT,

CAGC, TAGA, AGAA, AGAG, CATA, CAGT, CAGA, ACCT,

CTGT, ACAT, GOTT, GCTA, TCAG, CTTA, GGCC, ATTT,

CCCA, TATC, CCTG, TCTA, GCCT, ACTG, TGAG, GGTA,

CATT, TATT, CCAT, CCTC, CCAA, CTTT, TAAG, GCTG,

CCCT, TGAA, ACCA, GITT, TGTA, CTCA, GCCA, TATG,

GCAT, AAAG, AAAA, GGCT, TGAC, AGCA, TCTT, CTGA,

CATC, ACAA, GACA, AACA, CCCC, CACT, GGAG, GGCA,

TCAA, CAAG, TAAA, AAAT, TGCC, GGTT, GGGA, CCAC,

TGTG, CATG, TGCA, GAAT, TGTC, TGCT, CAAT, GGAA,

AGTG, TACT, CACA, TCCC
```

2-2. Nucleic Acid Fragment Size Selection

Figure 3:
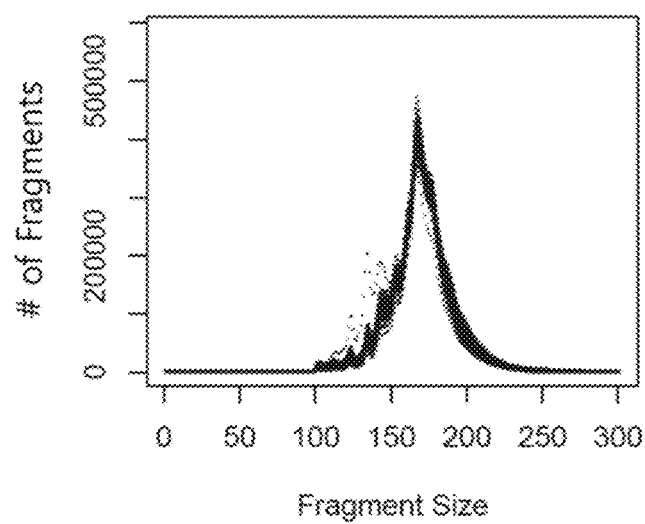
FIG. 3 is a graph illustrating size distributions of nucleic acid fragments selected according to an embodiment of the present invention.

Most of the nucleic acid fragments whose quality has been checked have a size in the range of 90 to 250, as shown in FIG. 3. Therefore, when a FEMS table including an area that is out of this size range, most areas are filled with zero (0) and only meaningless noise increases. For this reason, the nucleic acid fragment size was selected within this range.

Example 3. Production of Fragment End Motif Frequency and Size (FEMS) Table

Two-dimensional vectors were generated by plotting motif types on the X-axis and fragment sizes on the Y-axis to simultaneously express the end motif frequency and size information of the nucleic acid fragments selected in Example 2. More specifically, as shown in the left panel of FIG. 4, the type and size of nucleic acid motifs at both ends of one nucleic acid fragment are expressed as a frequency, and this is extended to the entire nucleic acid fragment and accumulated, to generate two-dimensional vectors as shown in FIG. 4.

Also, an edge summary was further performed by adding a column sum four times to the bottom of the two-dimensional vector in FIG. 4 in order to add frequency information for each fragment end motif irrelevant to the fragment size, and adding a row sum four times to the rightmost part of the two-dimensional vector of FIG. 4 in order to add the fragment size information irrelevant to the fragment end motif, to generate a two-dimensional vector as shown in the left panel of FIG. 5. The two-dimensional vector is defined as a fragment end motif frequency and size (FEMS) table. The FEMS table was visualized and an example thereof is shown in FIG. 5.

Example 3. CNN Model Construction and Training Process

A CNN artificial intelligence model that distinguished healthy subjects, liver cancer patients, and esophageal cancer patients was trained using the FEMS table two-dimensional vector as an input.

All the samples were divided into training, validation, and test datasets, the training dataset was used for model training, the validation dataset was used for hyper-parameter tuning, and the test dataset was used for final model testing. The number of samples for each set is as follows.

TABLE 2

| Dataset | Healthy subjects | Hepatocellular carcinoma patients | Esophageal cancer patients | Total |
|---------|------------------|-----------------------------------|----------------------------|-------|
| Train   | 193              | 26                                | 60                         | 279   |
| Valid   | 71               | 12                                | 22                         | 105   |
| Test    | 85               | 13                                | 26                         | 124   |
| Total   | 349              | 51                                | 108                        | 508   |

Figure 9:
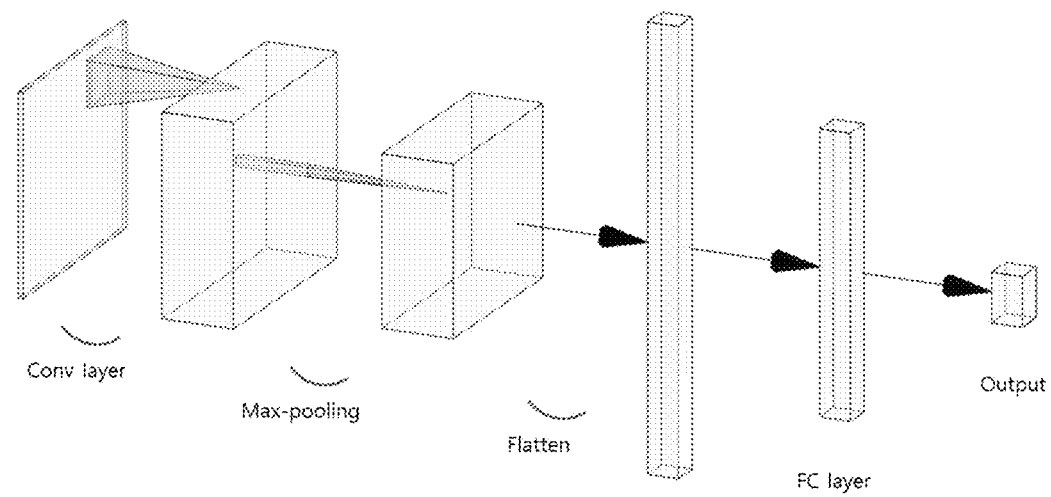
FIG. 9 is a schematic diagram illustrating the configuration of the CNN model constructed in an embodiment of the present invention.

The basic configuration of the CNN model is shown in FIG. 9. An ReLU (rectified linear unit) was used as an activation function, one convolution layer was used, and 5 10*10 patches were used. For the pooling method, a max mode and a 2×2 patch were used. One fully connected layer was used and 512 hidden nodes were included. Finally, the final DPI was calculated using the softmax function value.

The hyper-parameter tuning is a process of optimizing the values of various parameters (the number of convolution layers, the number of dense layers, the number of convolution filters, etc.) constituting the CNN model. The hyper-parameter tuning was performed using Bayesian optimization and grid search techniques. When the validation loss started to increase compared to training loss, it was considered that the model was overfitting and model training was stopped.

The performance of several models obtained through hyper-parameter tuning was compared using the validation dataset, the model having the best performance of the validation dataset was determined as the optimal model, and final performance evaluation was performed with the test dataset.

When the FEMS table 2D vector of a random sample was input to the model created through the above process, the probability that the sample is a healthy subject, the probability that the sample is a hepatocellular carcinoma patient and the probability that the sample is an esophageal cancer patient were calculated through the softmax function, which is the last layer of the CNN model. Such probability was defined as "deep probability index (DPI)".

A random sample is determined as a group having the highest DPI among the three types of DPIs. For example, when the DPIs of the healthy subject, the hepatocellular carcinoma liver patient, and the esophageal cancer patient calculated from the random sample are 0.6, 0.3, and 0.1, respectively, the sample was determined as the healthy subject.

Example 4. Evaluation of Performance of Constructed Deep-Learning Model 4-1 Evaluation of Performance (Test)

The performance of the DPI output from the deep learning model was tested. All samples were divided into training, validation, and test groups. The models were constructed using the training samples, and then the performance of the models constructed using the training samples was evaluated using the samples of the validation and test groups.

TABLE 3

|  | Accuracy | micro AUC |
|---|---|---|
| Train | 0.913 | 0.991 |
| Validation | 0.927 | 0.990 |
| Test | 0.895 | 0.955 |

Figure 7:
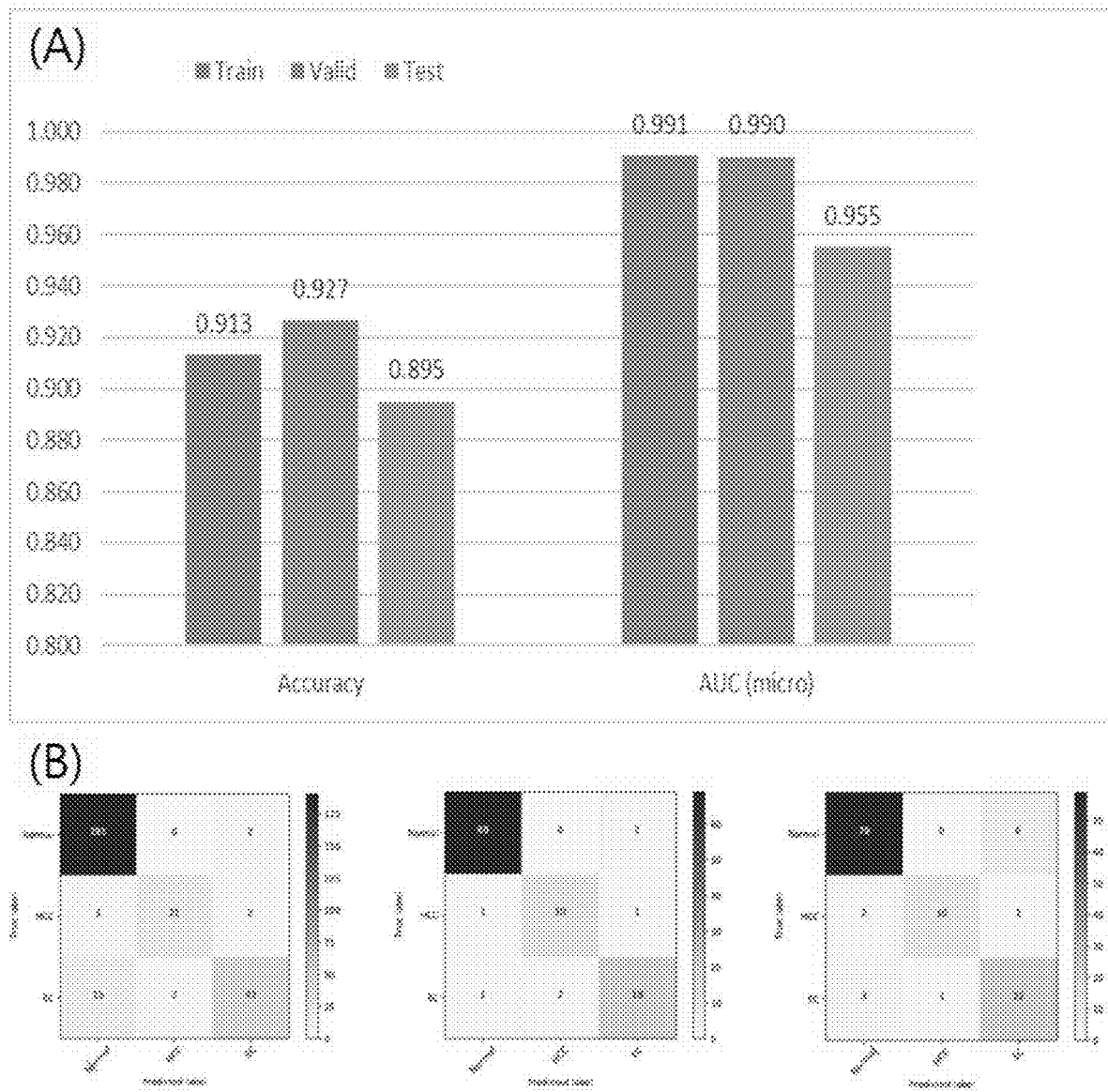
FIG. 7 in part (A) thereof shows the performance of the CNN model constructed according to an embodiment of the present invention, evaluated based on accuracy and micro-AUC, and FIG. 7 in part (B) thereof shows a confusion matrix.

As a result, as can be seen from Table 3 and FIG. 7, accuracy for Train, Valid, and Test groups was 91.3%, 92.7%, and 89.5%, respectively, and the micro AUCs, which were the results of multi-class ROC analysis, were 0.991, 0.990, and 0.955 in Train, Valid, and Test groups, respectively. FIG. 7A shows the performance of the CNN model evaluated based on accuracy and microAUC in the Train, Validation and Test groups, and FIG. 7B shows the performance of the CNN model evaluated based on the confusion matrix in the Train, Validation, and Test groups.

4-2. DPI Distribution

Figure 8:
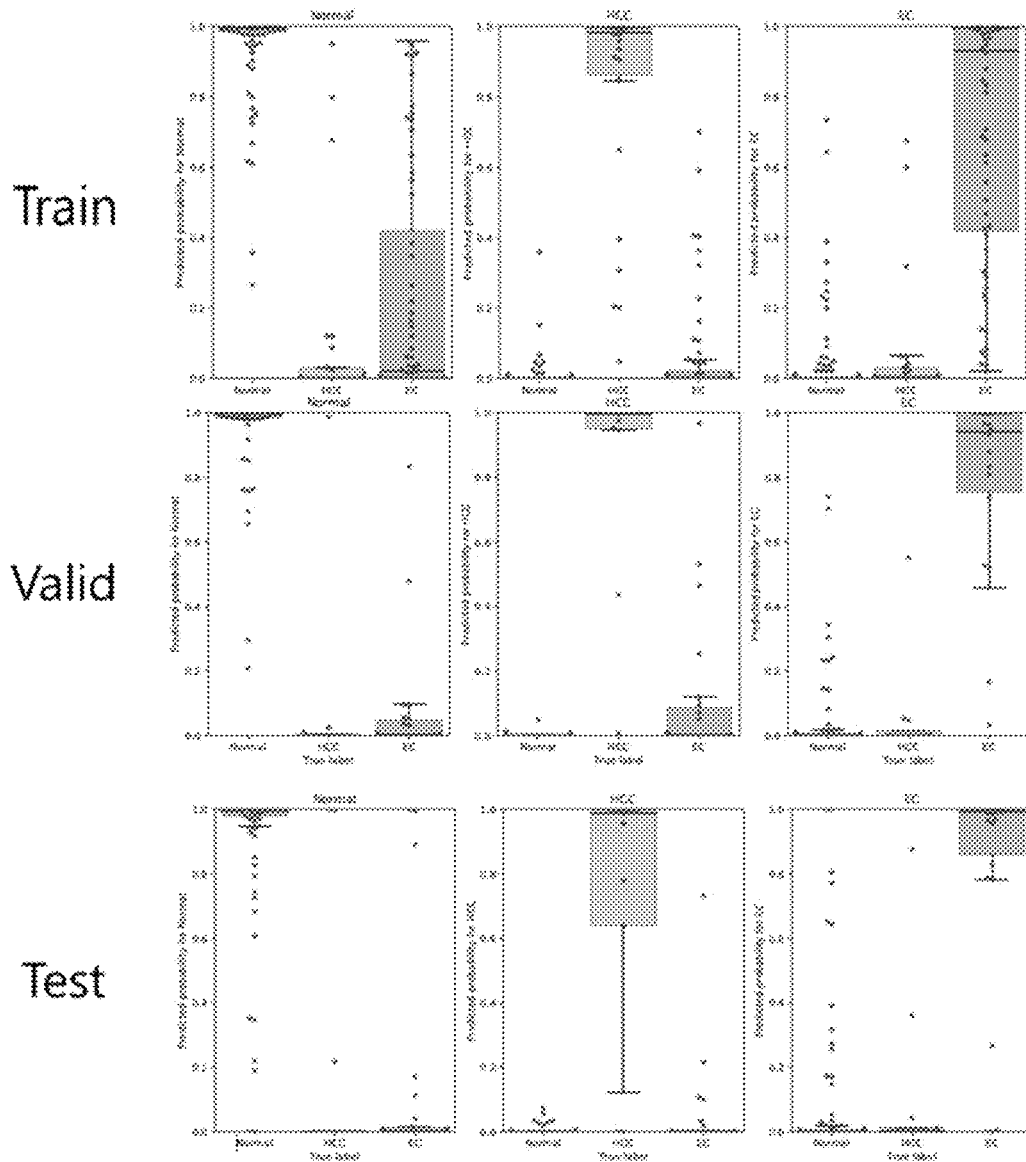
FIG. 8 shows how the probability values of healthy subjects, liver cancer patients, and esophageal cancer patients predicted by the CNN model constructed according to an embodiment of the present invention match actual patients, based on the distribution of DPIs output by the CNN model.

How much the DPI, which is the output value of the deep learning model constructed in Example 3, matched the actual patient was determined. In FIG. 8, an X-axis represents information of the actual sample (true label) and a Y-axis represents the DPIs of healthy subjects (Normal), hepatocellular carcinoma patients (HCC), and esophageal cancer patients (EC) calculated in the CNN model in this order from the left.

As a result, as can be seen from FIG. 8, the DPI distribution showed that in all of the Train, Validation, and Test datasets, the healthy subject samples had the highest probability of being healthy subjects, hepatocellular carcinoma patient samples had the highest probability of being hepatocellular carcinoma patients, and the esophageal cancer patent samples had the highest probability of being esophageal cancer patents.

Although specific configurations of the present invention have been described in detail, those skilled in the art will appreciate that this detailed description is provided as preferred embodiments for illustrative purposes and should not be construed as limiting the scope of the present invention. Therefore, the substantial scope of the present invention is defined by the accompanying filed claims and equivalents thereto.

INDUSTRIAL APPLICABILITY

The method for diagnosing cancer and predicting a cancer type using the end motif frequencies and sizes of cell-free nucleic acid fragments according to the present invention includes generating vectorized data and analyzing the same using an AI algorithm and thus is useful due to high sensitivity and accuracy thereof even in the case of low read coverage.

The invention claimed is:

1. A method for measuring fragment end motif frequency and size of nucleic acids, the method comprising:

a) extracting nucleic acids from a biological sample, the extracted nucleic acids comprising cell free DNA (cfDNA);

b) sequencing the nucleic acids to a depth of at least 1 million reads to obtain sequence reads;

c) aligning the sequence reads with a reference genome database, wherein the length of the reads is from 5 to 5,000 bp;

d) acquiring end motif frequencies and sizes of nucleic acid fragments based on the aligned sequence reads, wherein the end motif frequencies are selected from a total of 256 4-mer motifs, and wherein the nucleic acid fragments comprise fragment sizes ranging from 90 to 250 base pairs;

e) generating vectorized data using the end motif frequencies and sizes of nucleic acid fragments, wherein the vectorized data is expressed by a type of an end motif of the nucleic acid fragments and the size of the nucleic acid fragments plotted on a single or multidimensional axis;

f) inputting the generated vectorized data to a trained artificial intelligence model, wherein the artificial intelligence model transforms the vectorized data of step (e) into an output value, wherein the artificial intelligence model has been trained to adjust the output value to about 1 if there is cancer or to adjust the output value to about 0 if there is no cancer; and g) determining whether or not cancer develops, wherein the determining comprises comparing the output value of step (f) with a cut-off value to determine whether or not cancer develops, wherein if the output value is greater than a cut-off value, it is determined that there is cancer, and if the output value is less than the cut-off value, it is determined that there is no cancer, wherein the artificial intelligence model in step (f) has been trained to distinguish between vectorized data of a healthy subject and vectorized data of a cancer patient.

2. The method according to claim 1, wherein step (a) comprises:

a-i. obtaining nucleic acids from the blood, semen, vaginal cells, hair, saliva, urine, oral cells, amniotic fluid containing placental cells or fetal cells, tissue cells, or a mixture thereof;

a-ii. removing proteins, fats, and other residues from the collected nucleic acids using a salting-out method, a column chromatography method, or a bead method to obtain purified nucleic acids;

a-iii. producing a single-end sequencing or paired-end sequencing library for the purified nucleic acids or nucleic acids randomly fragmented by an enzymatic digestion, pulverization, or Hydroshear method;

a-iv. reacting the produced library with a next-generation sequencer; and a-v. obtaining sequence reads of the nucleic acids in the next-generation sequencer.

3. The method according to claim 1, wherein the end motif of each nucleic acid fragment in step (d) has a sequence pattern of 2 to 30 bases at both ends of the nucleic acid fragment.

4. The method according to claim 1, wherein the frequency of end motifs of the nucleic acid fragments in step (d) corresponds to the number of motifs detected in all the nucleic acid fragments.

5. The method according to claim 1, wherein the size of each nucleic acid fragment in step (d) corresponds to the number of bases from the 5' end to the 3' end of the nucleic acid fragment.

6. The method according to claim 1, wherein the vectorized data in step (d) is expressed by the type of the end motif of the nucleic acid fragment plotted on an X-axis and the size of the nucleic acid fragment plotted on a Y-axis.

7. The method according to claim 6, wherein the vectorized data further comprises a sum of frequencies for end motifs of nucleic acid fragments and a sum of frequencies for sizes of nucleic acid fragments.

8. The method according to claim 1, wherein the artificial intelligence model is a convolutional neural network (CNN).

9. The method according to claim 8, wherein, a loss function for performing binary classification is represented by Equation 1 below and a loss function for performing multi-class classification is represented by Equation 2 below:

Equation 1: Binary classification $$\text{loss}(\text{model}(x), y) = -\frac{1}{n}\left[\sum_{i=1}^{n}(y_i \log(\text{model}(x_i)) + (1 - y_y)\log(1 - \text{model}(x_i)))\right]$$

Model $(x_i)$=Artificial intelligence model output in response to $i^{th}$ input
y=Actual label value
n=Number of input data Equation 2: Multi-class classification $$\text{loss}(\text{model}(x), y) = -\frac{1}{n}\sum_{i=1}^{n}\left(\sum_{j=1}^{c}(y_{ij}\log(\text{model}(x_i))_j)\right)$$

Model $(x_i)_j = j^{th}$ artificial intelligence model output in response to $i^{th}$ input
y=Actual label value
n=Number of input data
c=Number of classes.

10. The method according to claim 1, wherein the output value resulting from analysis of the input vectorized data by the artificial intelligence model in step (f) is a deep probability index (DPI).

11. The method according to claim 1, wherein the cut-off value of step (e) is 0.5 and a determination is made that cancer has developed when the output value is 0.5 or more.

12. The method according to claim 1, wherein the artificial intelligence model is a deep neural network (DNN).

13. The method according to claim 1, wherein the artificial intelligence model is a recurrent neural network (RNN).

14. A non-transitory computer-readable storage medium comprising an instruction configured to be executed by a processor for diagnosing cancer through the following steps comprising:

(a) extracting nucleic acids from a biological sample to obtain sequence reads, the extracted nucleic acids comprising cell free DNA (cfDNA);

(b) aligning the sequence reads with a reference genome database;

(c) acquiring end motif frequencies and sizes of nucleic acid fragments based on the aligned sequence reads, wherein the end motif frequencies are selected from a total of 256 4-mer motifs, and wherein the nucleic acid fragments comprise fragment sizes ranging from 90 to 250 base pairs;

(d) generating vectorized data using the motif frequencies and sizes of nucleic acid fragments;

(e) inputting the generated vectorized data into a trained artificial intelligence model, wherein the artificial intelligence model transforms the vectorized data of step (d) into an output value, wherein the artificial intelligence model has been trained to adjust the output value to about 1 if there is cancer or to adjust the output value to about 0 if there is no cancer; and (f) determining whether or not cancer develops, wherein the determining comprises comparing the output value of step (e) with a cut-off value to determine whether or not cancer develops, wherein if the output value is greater than a cut-off value, it is determined that there is cancer, and if the output value is less than the cut-off value, it is determined that there is no cancer,
wherein the artificial intelligence model in step (f) has been trained to distinguish between vectorized data of a healthy subject and vectorized data of a cancer patient.

15. The non-transitory computer-readable storage medium of claim 14, further comprising predicting a cancer type, wherein the output value in step (e) comprises a deep probability index (DPI), wherein predicting a cancer type comprises comparing the DPI calculated for multiple cancer types, wherein the cancer type showing the highest DPI is predicted to be the cancer type of the sample.

16. A method for measuring fragment end motif frequency and size of nucleic acids, the method comprising:
   a) extracting nucleic acids from a biological sample, the extracted nucleic acids comprising cell free DNA (cfDNA);
   b) sequencing the nucleic acids to a depth of at least 1 million reads to obtain sequence reads;
   c) aligning the sequence reads with a reference genome database, wherein the length of the reads is from 5 to 5,000 bp;
   d) acquiring end motif frequencies and sizes of nucleic acid fragments based on the aligned sequence reads, wherein the end motif frequencies are selected from a total of 256 4-mer motifs, and wherein the nucleic acid fragments comprise fragment sizes ranging from 90 to 250 base pairs;
   e) generating vectorized data using the end motif frequencies and sizes of nucleic acid fragments, wherein the vectorized data is expressed by a type of an end motif of the nucleic acid fragments and the size of the nucleic acid fragments plotted on a single or multidimensional axis;
   f) inputting the generated vectorized data to a trained artificial intelligence model, wherein the artificial intelligence model transforms the vectorized data of step (e) into an output value, wherein the artificial intelligence model has been trained to adjust the output value to about 1 if there is cancer or to adjust the output value to about 0 if there is no cancer;
   g) determining whether or not cancer develops, wherein the determining comprises comparing the output value of step (f) with a cut-off value to determine whether or not cancer develops, wherein if the output value is greater than a cut-off value, it is determined that there is cancer, and if the output value is less than the cut-off value, it is determined that there is no cancer; and
   h) predicting a cancer type, wherein the output value in step (f) comprises a deep probability index (DPI), wherein predicting a cancer type comprises comparing the DPI calculated for multiple cancer types, wherein the cancer type showing the highest DPI is predicted to be the cancer type of the sample,
wherein the artificial intelligence model in step (f) has been trained to distinguish between vectorized data of a healthy subject and vectorized data of a cancer patient.

* * * * *

SEQUENCE LISTING

```
Sequence total quantity: 4
SEQ ID NO: 1             moltype = DNA  length = 15
FEATURE                  Location/Qualifiers
source                   1..15
                         mol_type = other DNA
                         organism = synthetic construct
SEQUENCE: 1
tacagactttt ggaat                                                     15

SEQ ID NO: 2             moltype = DNA  length = 15
FEATURE                  Location/Qualifiers
source                   1..15
                         mol_type = other DNA
                         organism = synthetic construct
SEQUENCE: 2
atgactgaaa cctta                                                      15

SEQ ID NO: 3             moltype = DNA  length = 18
FEATURE                  Location/Qualifiers
source                   1..18
                         mol_type = other DNA
                         organism = synthetic construct
SEQUENCE: 3
tacagactag tttggaat                                                   18

SEQ ID NO: 4             moltype = DNA  length = 18
FEATURE                  Location/Qualifiers
source                   1..18
                         mol_type = other DNA
                         organism = synthetic construct
SEQUENCE: 4
atgactgatc aaacctta                                                   18
```